United States Patent
Jaman et al.

(10) Patent No.: US 9,157,828 B2
(45) Date of Patent: Oct. 13, 2015

(54) METHOD AND APPARATUS FOR DIFFERENTIAL VOLTAGE GRID-BASED MOISTURE MONITORING OF STRUCTURES

(75) Inventors: Gregory Peter Jaman, Surrey (CA); Gamal Kazim Mustapha, Surrey (CA); Jason G. Teetaert, Vancouver, CA (US)

(73) Assignee: SMT RESEARCH LTD., Vancouver (CA)

(*) Notice: Subject to any disclaimer, the term of this patent is extended or adjusted under 35 U.S.C. 154(b) by 488 days.

(21) Appl. No.: 13/492,632

(22) Filed: Jun. 8, 2012

(65) Prior Publication Data

US 2012/0313652 A1 Dec. 13, 2012

Related U.S. Application Data

(60) Provisional application No. 61/494,581, filed on Jun. 8, 2011.

(51) Int. Cl.
G01M 3/16 (2006.01)
G01N 27/04 (2006.01)

(52) U.S. Cl.
CPC .............. *G01M 3/16* (2013.01); *G01N 27/048* (2013.01)

(58) Field of Classification Search
None
See application file for complete search history.

(56) References Cited

U.S. PATENT DOCUMENTS

| 5,081,422 | A  | * | 1/1992  | Shih ........................... 324/693 |
| 5,357,202 | A  | * | 10/1994 | Henderson ................ 324/557 |
| 5,540,085 | A  | * | 7/1996  | Sakata et al. .............. 73/49.2 |
| 5,850,144 | A  |   | 12/1998 | Howells et al. |
| 7,554,345 | B2 |   | 6/2009  | Vokey |
| 7,652,481 | B2 |   | 1/2010  | Vokey |
| 7,872,479 | B2 |   | 1/2011  | Lorenz et al. |
| 2009/0044595 | A1 | * | 2/2009 | Vokey ....................... 73/1.17 |

FOREIGN PATENT DOCUMENTS

| CA | 2599087 | 2/2008 |
| CA | 2689166 | 6/2011 |

* cited by examiner

*Primary Examiner* — Melissa Koval
*Assistant Examiner* — Courtney McDonnough
(74) *Attorney, Agent, or Firm* — Nexus Law Group LLP; Nicholas P. Toth

(57) ABSTRACT

A method and apparatus for differential voltage grid-based moisture monitoring of structures is provided. The method involves detecting a defect in a structural component, the structural component comprising a membrane for fluid impermeability, a deck for supporting the membrane, and a plurality of electrically conductive elements adjacent the membrane and electrically insulated from each other, by sensing the potential difference between a first element of the plurality of elements and a second element of the plurality of elements separated from the first element when there is an electrical potential between the deck and an electrically conductive fluid in contact with the first and second elements. The apparatus includes a switching circuit for connecting a voltage measuring circuit to the first and second elements, the voltage measuring circuit being operable to sense the potential difference between the first and second elements.

20 Claims, 4 Drawing Sheets

METHOD AND APPARATUS FOR DIFFERENTIAL VOLTAGE GRID-BASED MOISTURE MONITORING OF STRUCTURES

BACKGROUND OF THE INVENTION

1. Field of Invention

This invention relates to civionics and, in particular, to a method and apparatus for differential voltage grid-based moisture monitoring of structures.

2. Description of Related Art

A conventional low-sloped roof includes a roof deck, such as may be made of concrete or similar building material, a water impermeable membrane assembly on top of the roof deck, and optionally overburden, such as may be formed of aggregate material, laid on top of the membrane assembly.

Some conventional roofs include a grid of longitudinally and laterally disposed electrically conductive wires or tape which are electrically insulated from each other. The grid is installed above the membrane assembly and beneath the overburden, for the purpose of detecting moisture ingress into the building structure through defects in the membrane assembly. Such moisture ingress detection relies on the moisture present on the roof including elemental ions which create a detectable electrical current when the ions flow through a defect.

Canadian patent No. 2,599,087 issued to Vokey discloses a method of locating a defect in a roof comprising generating an applied voltage having a positive attached to the roof deck and a negative attached to at least one of the grid wires, and sensing at each of the wires in turn the electrical current flowing through the wire being sensed in response to the applied voltage. However, the method of Vokey relies on a measurement of electrical current through a grid wire rather than a measurement of the electrical current flow of the elemental ions flowing within moisture present on the roof.

An object of the invention is to address the above shortcomings.

SUMMARY

The above shortcomings may be addressed by providing, in accordance with one aspect of the invention, a method of detecting a defect in a structural component, the structural component comprising a membrane for fluid impermeability, a deck for supporting the membrane, and a plurality of electrically conductive elements adjacent the membrane and electrically insulated from each other. The method involves sensing the potential difference between a first element of the plurality of elements and a second element of the plurality of elements separated from the first element when there is an electrical potential between the deck and an electrically conductive fluid in contact with the first and second elements.

The method may involve generating the electrical potential between the deck and at least one element of the plurality of elements, the at least one element being different from the first and second elements, when the electrically conductive fluid is in electrical contact with the at least one element. The step of generating the electrical potential may involve generating the electrical potential between the deck and a drive pair of parallel, spaced apart elements of the plurality of elements when the drive pair is disposed on either side of the first and second elements. The step of generating the electrical potential may involve generating the electrical potential between the deck and a drive set of elements of the plurality of elements when the drive set circumscribes at least a portion of each of the first and second elements. The step of sensing the potential difference may involve sensing the potential difference between the first and second elements by a voltage measuring device when the voltage measuring device is selectably connected by a switching circuit to the first and second elements. The step of generating the electrical potential may involve generating the electrical potential by an electrical power generating circuit when the generating circuit is selectably connected by a switching circuit to the at least one element. The step of generating the electrical potential may involve generating the electrical potential by an electrical power generating circuit when the generating circuit is selectably connected by a switching circuit to the drive pair. The step of generating the electrical potential may involve generating the electrical potential by an electrical power generating circuit when the generating circuit is selectably connected by a switching circuit to the drive set. The method may involve sensing the potential difference between the first and second elements by a voltage measuring device when the generating circuit is generating the electrical potential and the voltage measuring device is selectably connected by the switching circuit to the first and second elements. The method may involve analyzing a plurality of the potential differences associated with a plurality of different pairs of the elements, respectively, for locating the defect. The method may involve determining electrical resistance between the first and second elements.

The method may involve selecting the first and second elements. Selecting the first and second elements may involve automatedly selecting the first and second elements. Selecting the first and second elements may involve selecting a sense pair of parallel, adjacently spaced apart elements of the plurality of elements.

The method may involve generating an electrical potential between the deck and at least one element of the plurality of elements, the at least one element being different from the first and second elements, the electrically conductive fluid being in electrical contact with the at least one element. Sensing the potential difference between a first element of the plurality of elements and a second element of the plurality of elements separated from the first element when there is an electrical potential between the deck and an electrically conductive fluid in contact with the first and second elements, may involve sensing the potential difference when the electrical potential is being generated.

The method may involve selecting the at least one element. Selecting the at least one element may involve automatedly selecting the at least one element. Selecting the at least one element may involve selecting a drive pair of parallel, spaced apart elements of the plurality of elements. Selecting a drive pair of parallel, spaced apart elements of the plurality of elements may involve selecting the drive pair such that the parallel, spaced apart elements of the drive pair are disposed on either side of the first and second elements. Selecting the drive pair such that the parallel, spaced apart elements of the drive pair are disposed on either side of the first and second elements may involve selecting the drive pair disposed on either side of the sense pair. Selecting the first and second elements may involve selecting the first and second elements disposed between the parallel, spaced apart elements of the drive pair. Selecting a sense pair of parallel, adjacently spaced apart elements of the plurality of elements may involve selecting the sense pair disposed between the parallel, spaced apart elements of the drive pair.

Selecting the at least one element may involve selecting a drive set of elements of the plurality of elements such that the drive set forms a quadrant defining a desired test area. Selecting a drive set of elements of the plurality of elements such that the drive set forms a quadrant defining a desired test area may involve selecting the drive set circumscribing at least a portion of each of the first and second elements. Selecting a drive set of elements of the plurality of elements such that the drive set forms a quadrant defining a desired test area may involve selecting the drive set circumscribing at least a portion of each of the parallel, adjacently spaced apart elements of the sense pair. Selecting the first and second elements may involve selecting the first and second elements disposed at least partly within the desired test area defined by the drive set. Selecting a sense pair of parallel, adjacently spaced apart elements of the plurality of elements may involve selecting the sense pair disposed at least partly within the desired test area defined by the drive set.

Generating an electrical potential between the deck and at least one element of the plurality of elements, the at least one element being different from the first and second elements, the electrically conductive fluid being in electrical contact with the at least one element, may involve generating the electrical potential between the deck and the drive pair. Generating an electrical potential between the deck and at least one element of the plurality of elements, the at least one element being different from the first and second, the electrically conductive fluid being in electrical contact with the at least one element, may involve generating the electrical potential between the deck and the drive set.

The method may involve connecting a voltage measuring device to the first and second elements. Connecting a voltage measuring device to the first and second elements may involve connecting the voltage measuring device to the sense pair.

The method may involve connecting a generator to the at least one element. Connecting a generator to the at least one element may involve connecting the generator to the drive pair. Connecting a generator to the at least one element may involve connecting the generator to the drive set.

The method may involve connecting a switching circuit to the plurality of elements. The method may involve connecting a switching circuit between the voltage measuring device and the first and second elements. The method may involve connecting a switching circuit between the voltage measuring device and the sense pair. The method may involve connecting a switching circuit between the generator and the at least one element. The method may involve connecting a switching circuit between the generator and the drive pair. The method may involve connecting a switching circuit between the generator and the drive set.

The method may involve switching a connection. Switching a connection may involve switching from a first sense connection between the voltage measuring device and the first and second elements to a second sense connection between the voltage measuring device and third and fourth elements of the plurality of elements. Switching a connection may involve switching from a first sense connection between the voltage measuring device and the sense pair to a second sense connection between the voltage measuring device and a second sense pair.

Switching a connection may involve switching from a first drive connection between the generator and the at least one element to a second drive connection between the generator and a different drive element of the plurality of elements. Switching a connection may involve switching from a first drive connection between the generator and the drive pair to a second drive connection between the generator and a different drive element of the plurality of elements. Switching from a first drive connection between the generator and the drive pair to a second drive connection between the generator and a different drive element of the plurality of elements may involve switching from the first drive connection to the second drive connection between the generator and a different drive pair. Switching from a first drive connection between the generator and the drive pair to a second drive connection between the generator and a different drive element of the plurality of elements may involve switching from the first drive connection to the second drive connection between the generator and the drive set.

Switching a connection may involve switching from a first drive connection between the generator and the drive set to a second drive connection between the generator and a different drive element of the plurality of elements. Switching from a first drive connection between the generator and the drive set to a second drive connection between the generator and a different drive element of the plurality of elements may involve switching from the first drive connection to the second drive connection between the generator and the drive pair. Switching from a first drive connection between the generator and the drive set to a second drive connection between the generator and a different drive element of the plurality of elements may involve switching from the first drive connection to the second drive connection between the generator and a different drive set.

The method may involve locating the defect by analyzing a plurality of sensed potential differences.

The method may involve wetting the surface of the membrane adjacent the plurality of elements.

In accordance with another aspect of the invention, there is provided an apparatus for detecting a defect in a structural component, the structural component comprising a membrane for fluid impermeability, a deck for supporting the membrane, and a plurality of electrically conductive elements adjacent the membrane and electrically insulated from each other. The apparatus includes a switching circuit for connecting a voltage measuring circuit to a first element of the plurality of elements and a second element of the plurality of elements separated from the first element, the voltage measuring circuit being operable to sense the potential difference between the first and second elements when there is an electrical potential between the deck and an electrically conductive fluid in contact with the first and second elements.

The apparatus may include an electrical power generating circuit for generating the electrical potential between the deck and at least one element of the plurality of elements, the at least one element being different from the first and second elements, when the electrically conductive fluid is in electrical contact with the at least one element. The switching circuit may be operable to selectably connect the generating circuit to the at least one element. The at least one element may include a drive pair of parallel, spaced apart elements of the plurality of elements. The drive pair may be disposed on either side of the first and second elements. The switching circuit may be operable to selectably connect the generating circuit to the drive pair. The at least one element may include a drive set of elements of the plurality of elements. The drive set may circumscribe at least a portion of each of the first and second elements. The switching circuit may be operable to selectably connect the generating circuit to the drive set. The apparatus may be operable to analyze a plurality of the potential differences associated with a plurality of different pairs of the elements, respectively, for locating the defect. The apparatus may be operable to determine electrical resistance between the first and second elements.

The apparatus may include a first switching circuit for connecting a voltage measuring circuit to a first element of the plurality of elements and a second element of the plurality of elements separated from the first element. The apparatus may include the voltage measuring circuit. The apparatus may be operable to sense the potential difference between the first and second elements when there is an electrical potential between the deck and an electrically conductive fluid in contact with the first and second elements. The first switching circuit may include a first plurality of switches. The first switching circuit may be operable to connect the voltage measuring circuit to a sense pair of parallel, adjacently spaced apart elements of the plurality of elements.

The apparatus may include a second switching circuit for connecting an electrical power generating circuit to at least one element of the plurality of elements. The apparatus may include the generating circuit. The apparatus may be operable to generate an electrical potential between the deck and the at least one element. The apparatus may be operable to generate an electrical potential between the deck and the at least one element, the at least one element being different from the first and second elements, when electrically conductive fluid is in electrical contact with the first and second elements and with the at least one element. The apparatus may be operable to sense the potential difference between the first and second elements when the electrical potential is being generated.

The second switching circuit may include a second plurality of switches. The second switching circuit may be operable to selectively connect the generating circuit to the at least one element such that the at least one element is different from the first and second elements.

The second switching circuit may be operable to connect the generating circuit to a drive pair of parallel, spaced apart elements of the plurality of elements. The second switching circuit may be operable to selectively connect the generating circuit to the drive pair such that each the parallel, spaced apart elements of the drive pair are disposed on either side of the first and second elements. The second switching circuit may be operable to selectively connect the generating circuit to the drive pair such that each the parallel, spaced apart elements of the drive pair are disposed on either side of the sense pair. The first switching circuit may be operable to selectively connect the voltage measuring circuit to the first and second elements such that the first and second elements are disposed between the parallel, spaced apart elements of the drive pair. The first switching circuit may be operable to selectively connect the voltage measuring circuit to the sense pair such that the sense pair is disposed between the parallel, spaced apart elements of the drive pair.

The second switching circuit may be operable to connect the generating circuit to a drive set of elements of the plurality of elements such that the drive set forms a quadrant defining a desired test area. The second switching circuit may be operable to selectively connect the generating circuit to the drive set such that the drive set circumscribes at least a portion of each of the first and second elements. The second switching circuit may be operable to selectively connect the generating circuit to the drive set such that the drive set circumscribes at least a portion of each of the parallel, adjacently spaced apart elements of the sense pair. The first switching circuit may be operable to selectively connect the voltage measuring circuit to the first and second elements such that the first and second elements are disposed at least partly within the desired test area defined by the drive set. The first switching circuit may be operable to selectively connect the voltage measuring circuit to the sense pair such that the sense pair is disposed at least partly within the desired test area defined by the drive set.

The apparatus may be operable to generate an electrical potential between the deck and the drive pair. The apparatus may be operable to generate an electrical potential between the deck and the drive pair when electrically conductive fluid is in electrical contact with the first and second elements and with the drive pair. The apparatus may be operable to generate an electrical potential between the deck and the drive set. The apparatus may be operable to generate an electrical potential between the deck and the drive set when electrically conductive fluid is in electrical contact with the first and second elements and with the drive set.

The apparatus may be operable to switch a connection. The apparatus may be operable to switch from a first sense connection between the voltage measuring circuit and the first and second elements to a second sense connection between the voltage measuring circuit and third and fourth elements of the plurality of elements. The third and fourth elements may include a second sense pair of parallel, adjacently spaced apart elements of the plurality of elements.

The apparatus may be operable to switch from a first drive connection between the generating circuit and the at least one element to a second drive connection between the generator and at least one different element of the plurality of elements. The at least one different element of the plurality of elements may include a second drive pair of parallel, spaced apart elements of the plurality of elements. The at least one different element of the plurality of elements may include a second drive set of elements of the plurality of elements such that the second drive set forms a second quadrant defining a second desired test area.

The apparatus may be operable to locate the defect by analyzing a plurality of sensed potential differences.

In accordance with another aspect of the invention, there is provided a use of the apparatus to sense the potential difference between the first and second elements when the apparatus includes the voltage measuring circuit. The use may include using the apparatus to analyze a plurality of the potential differences associated with a plurality of different pairs of the elements, respectively, for locating the defect.

Other aspects and features of the present invention will become apparent to those of ordinary skill in the art upon review of the following description of embodiments of the invention in conjunction with the accompanying figures and claims.

BRIEF DESCRIPTION OF THE DRAWINGS

In drawings which illustrate by way of example only embodiments of the invention.

DETAILED DESCRIPTION

An apparatus for detecting a defect in a structural component, the structural component comprising a membrane for fluid impermeability, a deck for supporting the membrane, and a plurality of electrically conductive elements adjacent the membrane and electrically insulated from each other, includes sensing means for sensing the potential difference between a first element of said plurality of elements and a second element of said plurality of elements separated from said first element when there is an electrical potential between the deck and an electrically conductive fluid in contact with said first and second elements. The apparatus may include first selecting means for selecting said first and second elements. The apparatus may include generating means for generating an electrical potential between the deck and at least one element of said plurality of elements, said at least one element being different from said first and second elements. The apparatus may include second selecting means for selecting said at least one element. The apparatus may include first connecting means for connecting said sensing means to said first and second elements. The apparatus may include second connecting means for connecting said generating means to said at least one element. The apparatus may include switching means for switching a connection.

Figure 1:
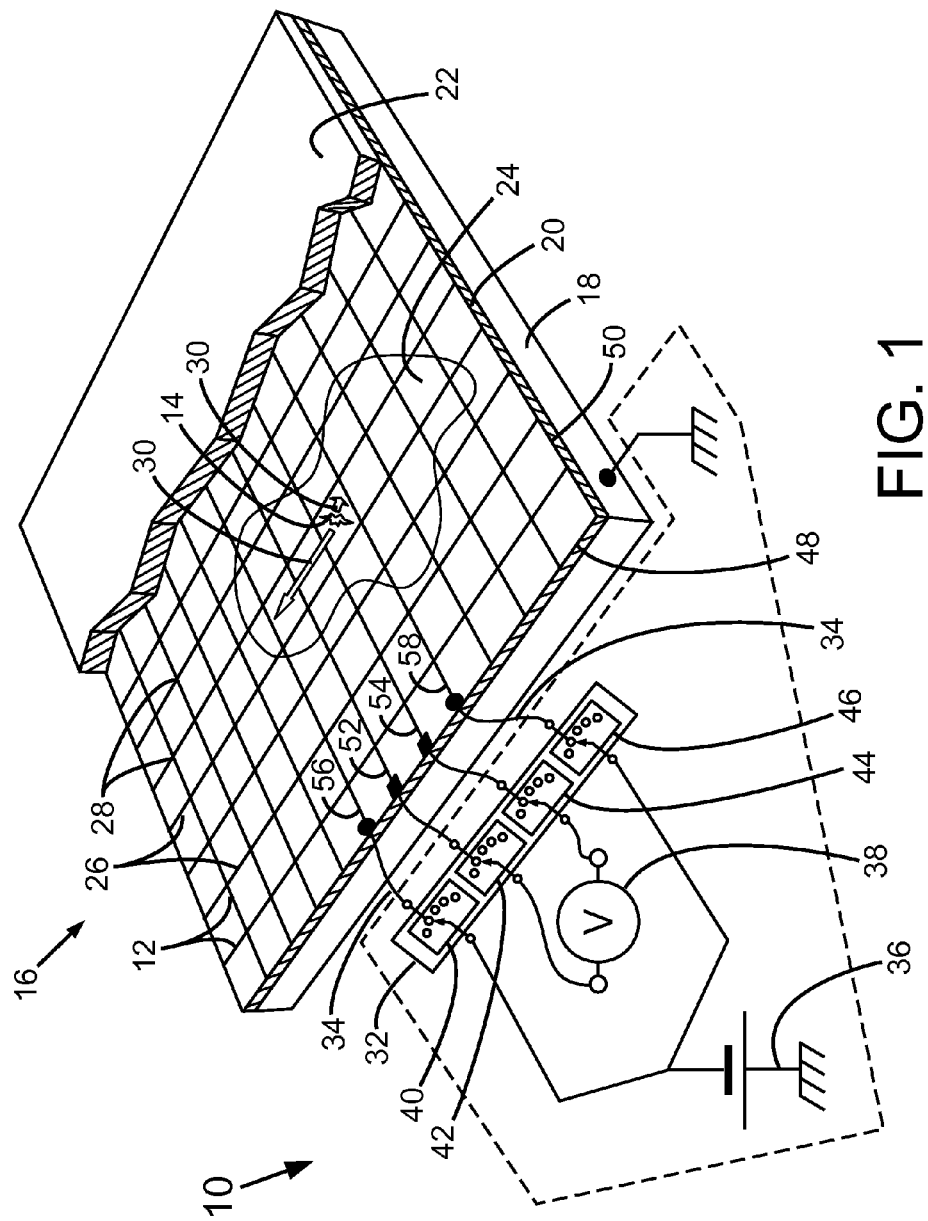
FIG. 1 is a schematic representation of an apparatus for detecting a defect in a structural component according to a first embodiment of the invention, showing a perspective view of the structural component.

Referring to FIG. 1, the apparatus according to a first and preferred embodiment of the invention is shown generally at 10 circumscribed by dashed line. The apparatus 10 functions to permit the use of a plurality of electrically conductive elements, such as the grid 12, in detecting a defect, such as the exemplary defect 14 shown in FIG. 1, of a structural component, such as the low-sloped building roof 16. As shown in FIG. 1, the roof 16 is composed of a roof deck 18, a membrane 20 supported by the roof deck 18, and overburden 22 covering the membrane 20. While the roof 16 of FIG. 1 is rectangular, in general the roof 16 may have any shape.

The membrane 20 may be any insulating layer that is intended to prevent moisture, such as the water 24 shown in FIG. 1, from penetrating and contacting the roof deck 18. The membrane 20 may include an assembly of insulating and related materials (not shown), for example.

The overburden 22 typically includes aggregate material and may include a binder, such as in the case of an asphalt-topped roof. In some situations, the overburden 22 includes top soil for supporting plant life. Preferably, the overburden 22, or at least a portion thereof, is fluid permeable to permit an electrically conductive fluid, such as the water 24, to penetrate through the overburden 22 to contact the upper surface of the membrane 20. While for clarity of illustration only a cut-out portion of the overburden 22 is shown in FIG. 1, the overburden 22 typically covers the entire membrane 20.

The grid 12 of FIG. 1 is formed of a number of electrically conductive wires 26 that are electrically insulated from each other at each junction 28. In some embodiments, the grid 12 is composed of electrically conductive tape. Other electrically conductive materials may be used to the form the grid 12. The wires 26 of FIG. 1 are electrically exposed to ions present within the water 24. When such ions flow, a measurable electrical current 30 results as indicated in FIG. 1 by the electrical current 30 arrows. The water 24 can be any electrically conductive fluid such as rain water, tap water, such as applied by hose (not shown), or any mixture of rain water and tap water for example. While the water 24 shown in FIG. 1 covers only a specific desired test area of the upper surface of the membrane 20, the water 24 is typically in contact with the entire upper surface of the membrane 20. While the wires 26 will typically form the rectilinear grid 12 as shown in FIG. 1, in general the wires 26 may be disposed in any suitable arrangement, including following any particular shape of the roof 16, may be spaced apart from each other by any desired distance or distances, and may form junctions 28 arranged in any desired pattern.

The apparatus 10 includes a switching circuit 32 suitable for connecting to the grid 12. In general, the switching circuit 32 is suitable for making any number of electrical connections to any number of wires 26 of the grid 12, and for disconnecting same. Connecting wires 34 connect between each of the wires 26 and respective connections of the switching circuit 32. For clarity of illustration, not all connecting wires 34 and not all connections of the switching circuit 32 are shown in the Figures. The connecting wires 34 may form part of the grid 12, may form part of the switching circuit 32, or any combination thereof for example.

In the first embodiment, the apparatus 10 includes an electrical power generating circuit, such as the source 36 shown in FIG. 1, and circuitry for detecting and measuring an electrical potential difference, such as the voltmeter 38 shown in FIG. 1. In some embodiments (not shown), the source 36, the voltmeter 38, or both the source 36 and the voltmeter 38, are not included in the apparatus 10. In such embodiments, the apparatus 10, the source 36 and the voltmeter 38 may be provided in a kit or otherwise provided separately in any combination thereof, for example. While for clarity of illustration one source 36 is shown in FIG. 1, any number of sources 36 may suitably be used to produce a potential difference between the roof deck 18 and wires 26 connected to the sources 36. While FIG. 1 shows the source 36 as a direct current (DC) source having a positive terminal electrically connected to the ground potential of the roof deck 18 and a negative terminal connected to switching circuit 32, the source 36 may be connected according to either desired polarity and may be operable to produce any desired electrical potential, including producing alternating current (AC), square, pulsed or other waveforms.

In the first embodiment shown in FIG. 1, the switching circuit 32 is operable to electrically connect the source 36 to the grid 12, such as by connecting the source 36 to any desired wire 26 or wires 26 of the grid 12. The switching circuit 32 is also operable to electrically connect the voltmeter 38 to the grid 12, such as by connecting the voltmeter 38 to a desired pair of adjacent wires 26.

The exemplary switching circuit 32 shown in FIG. 1 includes a first source switch 40, a first meter switch 42, a second meter switch 44, and a second source switch 46. In various embodiments, the switches 40 to 46 may be identical, similar, analogous or different to each other. For example, in some embodiments the switches 40 to 46 may suitably be used interchangeably. In some embodiments, the first and second source switches 40 and 46 are implemented by a single source switch (not shown) operable to simultaneously connect one or more sources, such as the source 36, to one or wires 26. In some embodiments, the first and second meter switches 42 and 44 are implemented by a single meter switch (not shown) operable to simultaneously connect the voltmeter 38 to any desired pair of wires 26. In some embodiments, the first and second meter switches 42 and 44 are implemented by a plurality of connections to the wires 26 permitting the voltmeter 38 to be manually connected to a desired pair of wires 26. In general, the switching circuit 32 may include any suitable number of switches.

While FIG. 1 shows one switching circuit 32, in general any number of switching circuits 32 may be employed. For example, separate switching circuits 32, which may be identical, similar, analogous or different to each other, may be employed for connecting between the source 36 and the grid 12 and for connecting between the voltmeter 38 and the grid 12. By way of further example, one switching circuit 32 may be employed for connecting to the grid 12 along the edge 48 of the roof 16 and a separate switching circuit 32 (not shown) may be employed for connecting to the grid 12 along the adjacent edge 50 of the roof 16. In some embodiments, however, a single switching circuit 32 is operable to connect to every wire 26 of the grid 12.

When the voltmeter 38 is connected to the first unpowered wire 52 and the second unpowered wire 54, the voltmeter 38 is operable to sense any potential difference, or voltage, present between the first and second unpowered wires 52 and 54. As can be appreciated by a person of ordinary skill in the art, a non-zero potential difference is indicative of electrical current 30 flowing from the first unpowered wire 52 to the second unpowered wire 54 or from the second unpowered wire 54 to the first unpowered wire 52, depending on the polarity of such non-zero potential difference.

Thus, there is provided an apparatus for detecting a defect in a structural component, the structural component comprising a membrane for fluid impermeability, a deck for supporting the membrane, and a plurality of electrically conductive elements adjacent the membrane and electrically insulated from each other, the apparatus comprising a switching circuit for connecting a voltage measuring circuit to a first element of said plurality of elements and a second element of said plurality of elements separated from said first element, the voltage measuring circuit being operable to sense the potential difference between said first and second elements when there is an electrical potential between the deck and an electrically conductive fluid in contact with said first and second elements.

Method of Operation

Still referring to FIG. 1, one or more of the wires 26 are selected for connecting to the source 36. In the exemplary use of the apparatus 10 shown in FIG. 1, a first powered wire 56 and a second powered wire 58 are selected for connecting to the source 36, and then connected to the source 36 via the switching circuit 32. When the source 36 is activated, an electrical potential is generated between the roof deck 18 and the first and second powered wires 56 and 58.

In other uses of the apparatus 10, only one wire 26 may be selected and connected to the source 36, for example. In a further use, four wires 26 may be selected to form a quadrant circumscribing a desired test area of the upper surface of the membrane 20. For example, the four outermost wires 26 of the grid 12 disposed along the edges of the roof 16 may be selected to form a quadrant circumscribing the entire upper surface of the membrane 20, for example. In general, the quadrant may be formed by any suitable number of wires 26 creating a closed path defining a desired test area having any shape.

With the first and second unpowered wires 52 and 54 selected and connected to the voltmeter 38 via the switching circuit 32, and with the source 36 generating a potential difference between the water 28 and the roof deck 18, any leakage of water 28 through the defect 14 toward the roof deck 18 will cause a measurable electrical current through the water 28 on the upper surface of the membrane 20. As indicated in FIG. 1, the electrical current 30 flows from the roof deck 18 at ground potential through the defect 14 and along the upper surface of the membrane 20 to the first and second powered wires 56 and 58. The electrical direction of the electrical current 30 flow will depend on the polarity of the electrical potential between the water 28 and the roof deck 18, which may be selected as either positive or negative polarity. When the electrical current 30 is flowing, a potential difference, or voltage, exists between spaced apart wires 26 lying in the path of the electrical current 30 in accordance with Ohm's law, as is known in the art. As indicated in FIG. 1, a non-zero magnitude of the voltage measured between the first and second unpowered wires 52 and 54 indicates the electrical current 30 is flowing, thereby detecting the presence of the defect 14. The location of the defect 14 in FIG. 1 is between the first and second powered wires 56 and 58.

Figure 2:
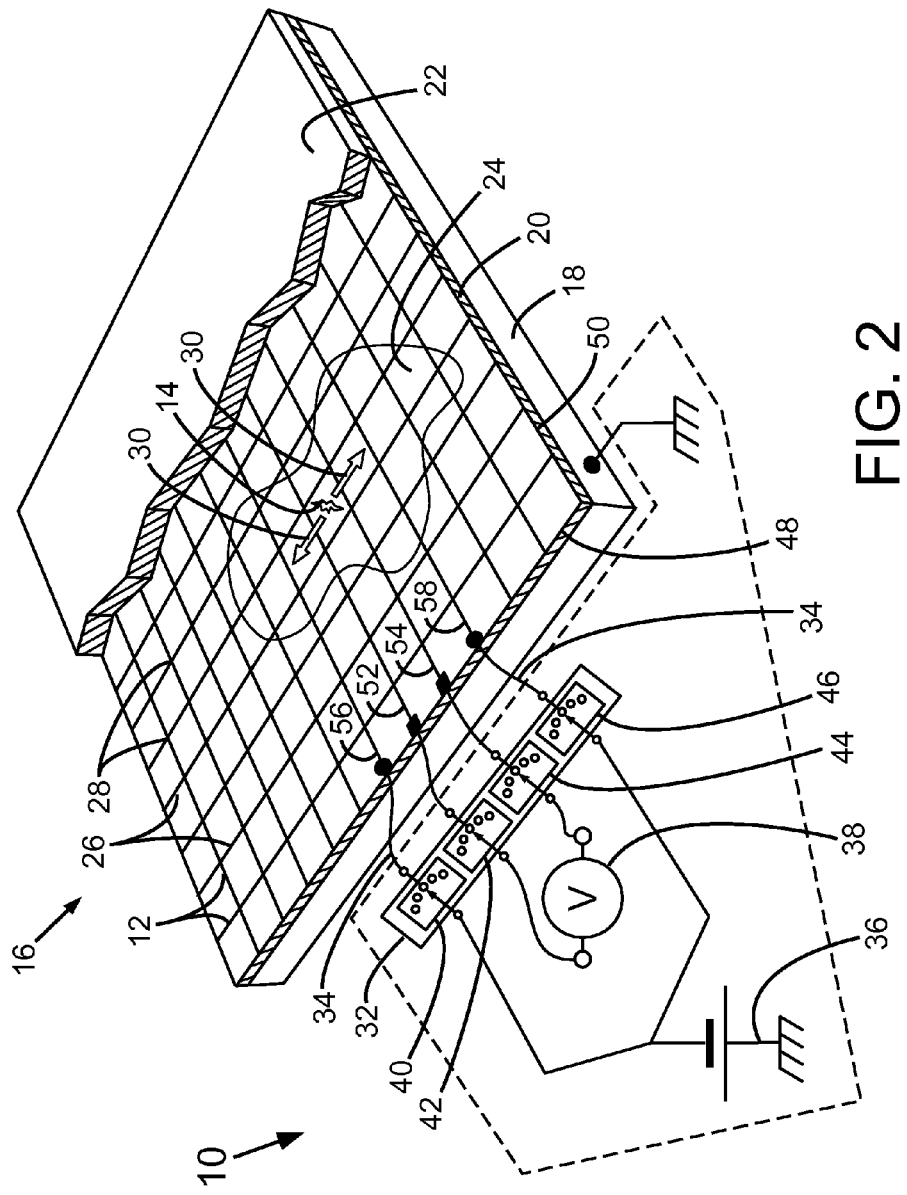
FIG. 2 is a schematic representation of the apparatus shown in FIG. 1 and a perspective view of the structural component shown in FIG. 1, showing a first switched set of electrical connections.
Figure 3:
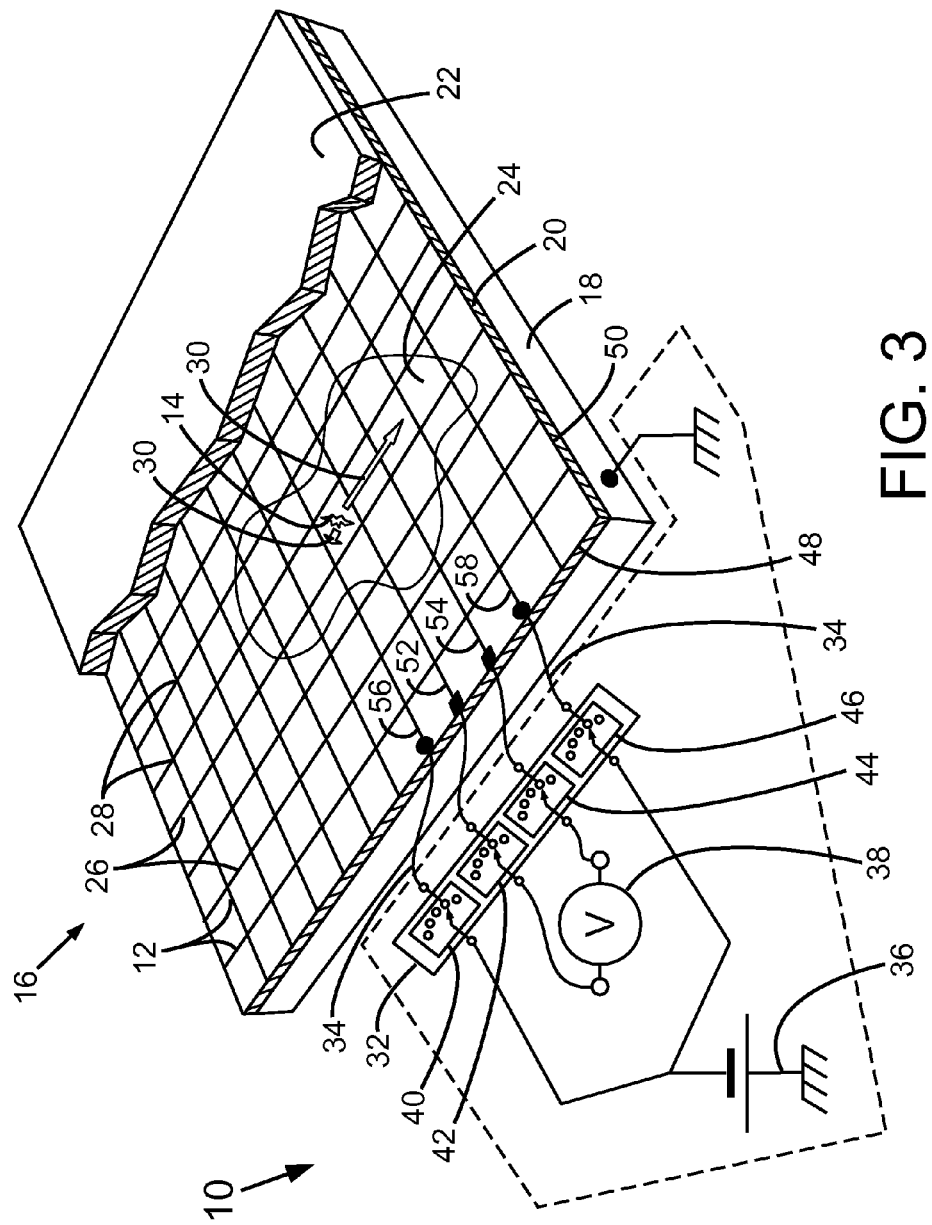
FIG. 3 is a schematic representation of the apparatus shown in FIG. 1 and a perspective view of the structural component shown in FIG. 1, showing a second switched set of electrical connections.

Referring to FIGS. 1 to 3, the defect 14 can be precisely located by switching connections and taking multiple measurements of the electrical current 30 through the water 28.

Referring to FIG. 2, when the first and second unpowered wires 52 and 54 straddle the defect 14, the current flow 30 is split between two approximately opposing directions, namely between the defect 14 and the first powered wire 56 and between the defect 14 and the second powered wire 58. Thus, the potential difference between the first and second unpowered wires 52 and 54, and hence the voltage measured by the voltmeter 38, is minimal or nil.

Referring to FIG. 3, when the first and second unpowered wires 52 and 54 are on a side of the defect 14 opposite to that shown in FIG. 1, then the electrical current 30 is approximately equal in magnitude and opposite in direction when compared to the electrical current 30 resulting from the arrangement shown in FIG. 1. Accordingly, the magnitude of the voltage measured by the voltmeter 38 is approximately equal in magnitude and opposite in polarity to the voltage that is measured in accordance with the arrangement shown in FIG. 1.

By analyzing the measured voltages obtained by the arrangements shown in FIGS. 1 to 3, it can be determined that the defect 14 lies between the first and second unpowered wires 52 and 54 of FIG. 2.

By switching connections along the roof 16 in a longitudinal direction along the edge 48 as shown in FIGS. 1 to 3 and then transversely (not shown) along the adjacent edge 50 in a similar manner, the defect 14 can be advantageously located within a single cell area defined by the grid 12, including when the defect 14 is located adjacent an edge of the roof 16.

In an exemplary variation, the wires 26 located at the outermost edges of the roof 16, or any closed path defining a desired test area (not shown), may be powered by the source 36. The potential difference between successively selected longitudinal and/or lateral pairs of adjacent unpowered wires 26 that lie at least partly within the desired test area are successively connected to the voltmeter 36 and their respective potential differences are measured without switching the powered connections defining the desired test area. The measured potential differences are analyzed to locate any defects present within the desired test area.

Thus, there is provided a method of detecting a defect in a structural component, the structural component comprising a membrane for fluid impermeability, a deck for supporting the membrane, and a plurality of electrically conductive elements adjacent the membrane and electrically insulated from each other, the method comprising sensing the potential difference between a first element of said plurality of elements and a second element of said plurality of elements separated from said first element when there is an electrical potential between the deck and an electrically conductive fluid in contact with said first and second elements.

Resistance Test

Figure 4:
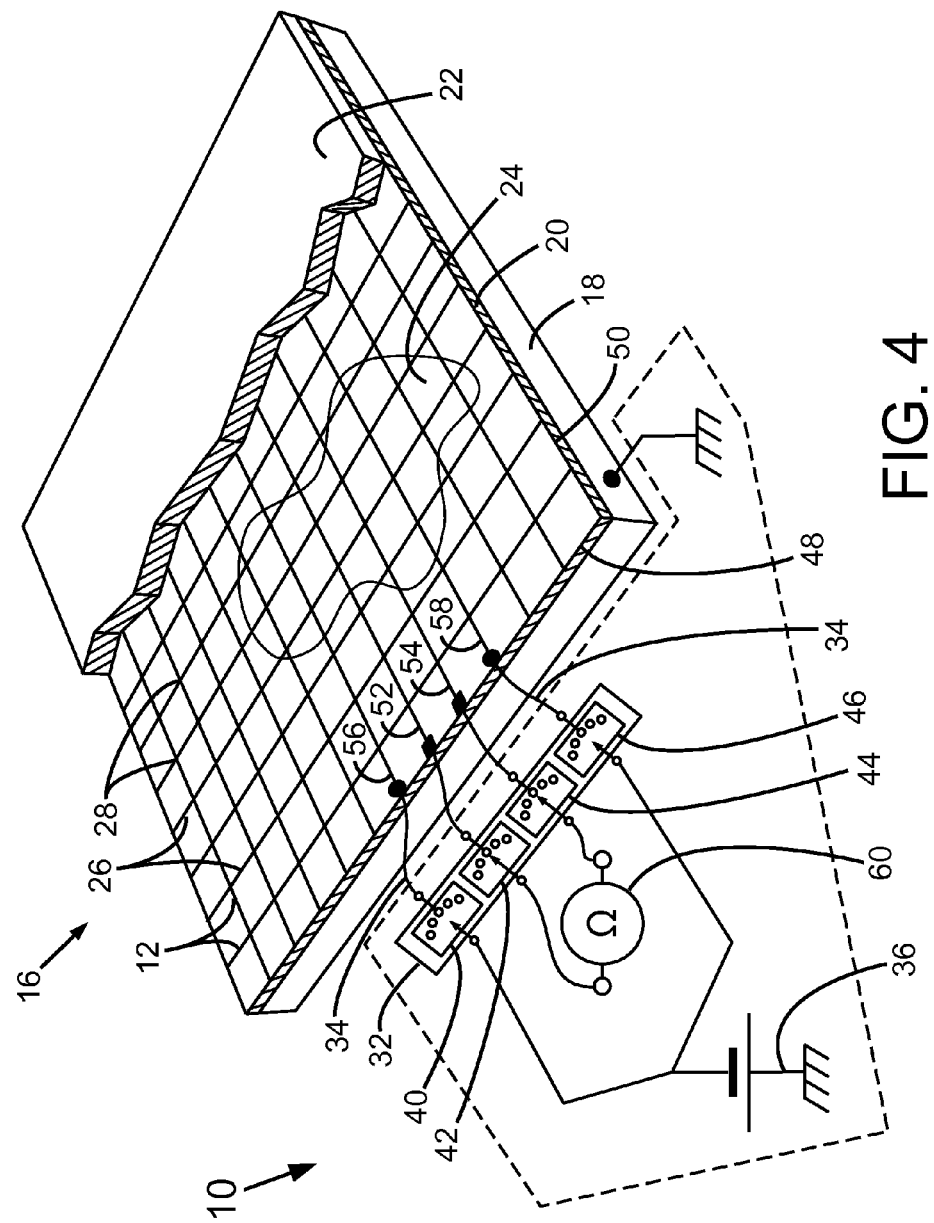
FIG. 4 is a schematic representation of the apparatus shown in FIG. 1 and a perspective view of the structural component shown in FIG. 1, showing a resistance test configuration of the apparatus.

Referring to FIG. 4, it may be desirable to determine whether the water 24 or other electrically conductive fluid is in electrical contact with one or more wires 26 at the upper surface of the membrane 20. This determination may be particularly desirable after at least some water 24 has been supplied from above the overburden 22, yet before attempting to locate any defects 14 (FIGS. 1 to 3), for example. If the electrical contact between the wires 26 via the water 24 is inadequate, more water 24 can be supplied to further penetrate the overburden 22 and to better provide electrical contact between the wires 26, for example.

In the exemplary configuration shown in FIG. 4, an ohmmeter 60 is connected via the first and second meter switches 42 and 44 to the first and second unpowered wires 52 and 54. The electrical resistance between the two unpowered wires 52 and 54 indicates the extent to which electrical contact is being made between each of the unpowered wires 52 and 54 and the water 24, and between the unpowered wires 52 and 54 via the water 24. FIG. 4 shows the source 36 disconnected from all the wires 26 of the grid 12 by being disconnected at the first and second source switches 40 and 46.

As will be appreciated by a person skilled in the art, dry conditions causing poor physical contact between the water 24 and either or both of the unpowered wires 52 and 54 will produce a large electrical resistance between the unpowered wires 52 and 54. Such large electrical resistance can be measured by use of the ohmmeter 60, thereby indicating that more water 24 needs to be applied to the upper surface of the membrane 20 via the overburden 22. On the other hand, a measurement by the ohmmeter 60 showing a small electrical resistance, or high electrical conductivity, between the unpowered wires 52 and 54 indicates there is good physical contact between the water 24 and both of the unpowered wires 52 and 54.

By appropriate use of the switching circuit 32, the electrical resistance between various pairs of unpowered wires 26 can be measured by the ohmmeter 60. In this manner, it is possible to test whether the water 24 is adequately in contact with the entire upper surface of the membrane 20 and all of the wires 26 of the grid 12. Such test can be performed whether or not any defect (not shown in FIG. 4) in the membrane 20 is present.

While FIG. 4 shows use of the ohmmeter 60, any suitable technique for determining the electrical resistance or conductivity of a plurality of the wires 26 may be employed. For example, the source 36 may be connected (not shown) between two wires 26 (as opposed to being connected between one or more wires 26 and the roof deck 18) and the electrical current through the completed circuit above the membrane 20 can be measured as an indication of conductivity between the two connected wires 26. By way of further example, a time-domain reflectometer, or TDR, (not shown) may be employed to determine specific points of high electrical resistance along a completed circuit of wires 26 above the membrane 20, thereby indicating points along one or more wires 26 where electrical contact with the water 24 is inadequate.

While embodiments of the invention have been described and illustrated, such embodiments should be considered illustrative of the invention only. The invention may include variants not described or illustrated herein in detail. For example, the present invention may be suitably applied to a structural component which is a floor, ceiling or foundation of a building or other structure. Thus, the embodiments described and illustrated herein should not be considered to limit the invention as construed in accordance with the accompanying claims.

What is claimed is:

1. A method of detecting a defect in a structural component, the structural component comprising a membrane for fluid impermeability, a deck for supporting the membrane, and a plurality of electrically conductive elements adjacent the membrane and electrically insulated from each other, the method comprising:

(a) determining electrical resistance between respective said elements of each of a plurality of pairs of said elements disposed at an upper surface of the membrane opposite the deck;

(b) supplying an electrically conductive fluid to the membrane at said upper surface until determining by step (a) that said electrically conductive fluid is in contact with a first said element, a second said element separate from said first element, and at least one said element other than said first and second elements; and then (c) sensing the potential difference between said first and second elements when an electrical power generating circuit is selectably connected by a switching circuit to said at least one element such that said generating circuit is generating an electrical potential between the deck and said electrically conductive fluid.

2. The method of claim 1 wherein determining electrical resistance between respective said elements of each of a plurality of pairs of said elements disposed at an upper surface of the membrane opposite the deck comprises: determining said electrical resistance when said plurality of pairs comprise every one of said plurality of elements.

3. The method of claim 2 wherein sensing the potential difference between said first and second elements when an electrical power generating circuit is selectably connected by a switching circuit to said at least one element such that said generating circuit is generating an electrical potential between the deck and said electrically conductive fluid comprises: sensing the potential difference when said generating circuit is connected to a drive pair of parallel, spaced apart elements of said plurality of elements and when said drive pair is disposed on either side of said first and second elements.

4. The method of claim 2 wherein sensing the potential difference between said first and second elements when an electrical power generating circuit is selectably connected by a switching circuit to said at least one element such that said generating circuit is generating an electrical potential between the deck and said electrically conductive fluid comprises: sensing the potential difference when said generating circuit is connected to a drive set of said elements circumscribing at least a portion of each of said first and second elements.

5. The method of claim 1 wherein determining electrical resistance between respective said elements of each of a plurality of pairs of said elements disposed at an upper surface of the membrane opposite the deck comprises: determining said electrical resistance by an ohmmeter successively connected via said switching circuit to said each pair; and wherein sensing the potential difference between said first and second elements when an electrical power generating circuit is selectably connected by a switching circuit to said at least one element such that said generating circuit is generating an electrical potential between the deck and said electrically conductive fluid comprises: sensing the potential difference by a voltage measuring device connected by said switching circuit to said first and second elements.

6. The method of claim 2 wherein supplying an electrically conductive fluid to the membrane at said upper surface until determining by step (a) that said electrically conductive fluid is in contact with a first said element, a second said element separate from said first element, and at least one said element other than said first and second elements comprises: determining that said electrically conductive fluid is in contact with every one of said plurality of elements.

7. The method of claim 6 wherein sensing the potential difference between said first and second elements when an electrical power generating circuit is selectably connected by a switching circuit to said at least one element such that said generating circuit is generating an electrical potential between the deck and said electrically conductive fluid comprises: sensing the potential difference when said generating circuit is connected to a drive pair of parallel, spaced apart elements of said plurality of elements and when said drive pair is disposed on either side of said first and second elements.

8. The method of claim 6 wherein sensing the potential difference between said first and second elements when an electrical power generating circuit is selectably connected by a switching circuit to said at least one element such that said generating circuit is generating an electrical potential between the deck and said electrically conductive fluid comprises: sensing the potential difference when said generating circuit is connected to a drive set of said elements circumscribing at least a portion of each of said first and second elements.

9. The method of claim 6 wherein determining electrical resistance between respective said elements of each of a plurality of pairs of said elements disposed at an upper surface of the membrane opposite the deck comprises: determining said electrical resistance by an ohmmeter successively connected via said switching circuit to said each pair; and wherein sensing the potential difference between said first and second elements when an electrical power generating circuit is selectably connected by a switching circuit to said at least one element such that said generating circuit is generating an electrical potential between the deck and said electrically conductive fluid comprises: sensing the potential difference by a voltage measuring device connected by said switching circuit to said first and second elements.

10. The method of claim 9 further comprising analyzing a plurality of the potential differences associated with a plurality of different pairs of said elements, respectively, for locating the defect.

11. The method of claim 7 wherein determining electrical resistance between respective said elements of each of a plurality of pairs of said elements disposed at an upper surface of the membrane opposite the deck comprises: determining said electrical resistance by an ohmmeter successively connected via said switching circuit to said each pair; wherein sensing the potential difference between said first and second elements when an electrical power generating circuit is selectably connected by a switching circuit to said at least one element such that said generating circuit is generating an electrical potential between the deck and said electrically conductive fluid comprises: sensing the potential difference by a voltage measuring device connected by said switching circuit to said first and second elements; and further comprising analyzing a plurality of the potential differences associated with a plurality of different pairs of said elements, respectively, for locating the defect.

12. An apparatus for detecting a defect in a structural component, the structural component comprising a membrane for fluid impermeability, a deck for supporting the membrane, and a plurality of electrically conductive elements adjacent the membrane and electrically insulated from each other, the apparatus comprising:
(a) an electrical power generating circuit; and
(b) a switching circuit operable to connect an ohmmeter to each of a plurality of pairs of said elements disposed at an upper surface of the membrane opposite the deck such that the ohmmeter is operable to successively determine electrical resistance between respective said elements of said each pair until determinations of said electrical resistance by the ohmmeter indicate that an electrically conductive fluid supplied to the membrane at said upper surface is in contact with a first said element, a second said element separate from said first element, and at least one said element other than said first and second elements; said switching circuit being operable to subsequently connect a voltage measuring circuit to said first and second elements such that the voltage measuring circuit is operable to sense the potential difference between said first and second elements when said switching circuit is selectably connecting said generating circuit to said at least one element such that said generating circuit is generating an electrical potential between the deck and said electrically conductive fluid.

13. The apparatus of claim 12 wherein said switching circuit is operable to connect the ohmmeter to said each pair until said determinations by the ohmmeter indicate that said electrically conductive fluid is in contact with every one of said plurality of elements.

14. The apparatus of claim 12 wherein said at least one element comprises a drive pair of parallel, spaced apart elements of said plurality of elements, said drive pair being disposed on either side of said first and second elements, said switching circuit being operable to selectably connect said generating circuit to said drive pair.

15. The apparatus of claim 13 wherein said at least one element comprises a drive pair of parallel, spaced apart elements of said plurality of elements, said drive pair being disposed on either side of said first and second elements, said switching circuit being operable to selectably connect said generating circuit to said drive pair.

16. The apparatus of claim 13 wherein said at least one element comprises a drive set of said elements, said drive set circumscribing at least a portion of each of said first and second elements, said switching circuit being operable to selectably connect said generating circuit to said drive set.

17. The apparatus of claim 13 wherein the apparatus is operable to analyze a plurality of the potential differences associated with a plurality of different pairs of said elements, respectively, for locating the defect.

18. The apparatus of claim 15 wherein the apparatus is operable to analyze a plurality of the potential differences associated with a plurality of different pairs of said elements, respectively, for locating the defect, the apparatus comprising said ohmmeter and said voltage measuring circuit.

19. Use of the apparatus of claim 12 to determine said electrical resistance in conjunction with supplying said electrically conductive fluid until determining that said electrically conductive fluid is in contact with said first element, said second element, and said at least one element, and then to sense the potential difference between said first and second elements.

20. Use as defined in claim 19 further comprising using the apparatus to determine said electrical resistance in conjunction with supplying said electrically conductive fluid until determining that said electrically conductive fluid is in contact with every one of said plurality of elements, and then to analyze a plurality of the potential differences associated with a plurality of different pairs of said elements, respectively, for locating the defect.

* * * * *